United States Patent
Barnett

[11] Patent Number: 6,011,987
[45] Date of Patent: Jan. 4, 2000

[54] FIDUCIAL POSITIONING CUP

[75] Inventor: Gene H. Barnett, Gates Mills, Ohio

[73] Assignee: The Cleveland Clinic Foundation, Cleveland, Ohio

[21] Appl. No.: 08/986,863

[22] Filed: Dec. 8, 1997

[51] Int. Cl.[7] .................................................... A61B 5/00
[52] U.S. Cl. ........................ 600/414; 606/130; 600/426
[58] Field of Search .................................. 600/410, 414, 600/407, 426; 128/899; 606/116, 130; 901/46; 395/89, 86, 93; 378/205, 207

[56] References Cited

U.S. PATENT DOCUMENTS

| | | |
|---|---|---|
| 4,344,183 | 8/1982 | Jacobson . |
| 4,826,487 | 5/1989 | Winter . |
| 5,024,727 | 6/1991 | Campbell et al. ...................... 156/663 |
| 5,074,318 | 12/1991 | Campbell et al. ...................... 128/899 |
| 5,193,106 | 3/1993 | DeSena . |
| 5,195,526 | 3/1993 | Michelson . |
| 5,263,956 | 11/1993 | Nobles . |
| 5,368,030 | 11/1994 | Zinreich et al. . |
| 5,394,457 | 2/1995 | Leibinger et al. . |
| 5,397,329 | 3/1995 | Allen ......................................... 606/73 |
| 5,408,409 | 4/1995 | Glassman et al. . |
| 5,469,847 | 11/1995 | Zinreich et al. . |
| 5,517,990 | 5/1996 | Kalfas et al. .......................... 128/653.1 |
| 5,551,429 | 9/1996 | Fitzpatrick et al. .................. 128/653.1 |
| 5,575,794 | 11/1996 | Walus et al. ............................. 606/116 |
| 5,622,187 | 4/1997 | Carol . |
| 5,695,501 | 12/1997 | Carol et al. ............................. 606/130 |
| 5,732,703 | 3/1998 | Kalfas et al. .......................... 128/653.1 |
| 5,769,789 | 6/1998 | Wang et al. . |
| 5,792,147 | 8/1998 | Evans et al. . |
| 5,807,252 | 9/1998 | Hassfeld . |
| 5,852,647 | 12/1998 | Schick et al. . |
| 5,878,104 | 3/1999 | Ploetz . |

FOREIGN PATENT DOCUMENTS

WO 94/17733   8/1994   WIPO .

OTHER PUBLICATIONS

Article entitled: "Computer–Assisted Coregistration of Multislice SPECT and MR Brain Images by Fixed External Fiducials," by Robert T. Malison et al. Published in the *Journal of Computer Assisted Tomography*, vol. 17, No. 6, 1993.

*Primary Examiner*—Marvin M. Lateef
*Assistant Examiner*—Shawna J. Shaw
*Attorney, Agent, or Firm*—Fay, Sharpe, Fagan, Minnich & McKee, LLP

[57] ABSTRACT

A fiducial positioning cup (86) has a hemispherical well (92) in its top and a central bore (94) from a bottom of the hemispherical well (92) to a base of the positioning cup (86). The fiducial cup (86) is then attached to the skin (88) of a patient. A needle (110) is passed through the fiducial positioning cup (86) to mark an area of the patient's skin (88) with a tattoo (112). Fiducials (84) are secured in the fiducial positioning cups (86). Magnetic resonance or other diagnostic images are taken. Once the images are taken, the fiducials (84) and fiducial positioning cups (86) are removed. The tattoo mark (112) remains. The fiducial positioning cups (86) are reattached when a stereotactic procedure is to be performed. The needle (110) is passed through the fiducial cups (86) and a tip of the needle (110) is aligned with the tattooed mark (112) on the patient's skin (88). The fiducial cup (86) is then lowered and centered over the tattooed mark (112). A stereotactic wand (36) is aligned with the magnetic resonance image by placing a tip (42) of the wand (36) in the fiducial cups (86) and emitting signals. The stereotactic system decodes the signals to identify where the tip (42) of the wand (36) is on the magnetic resonance image.

16 Claims, 5 Drawing Sheets

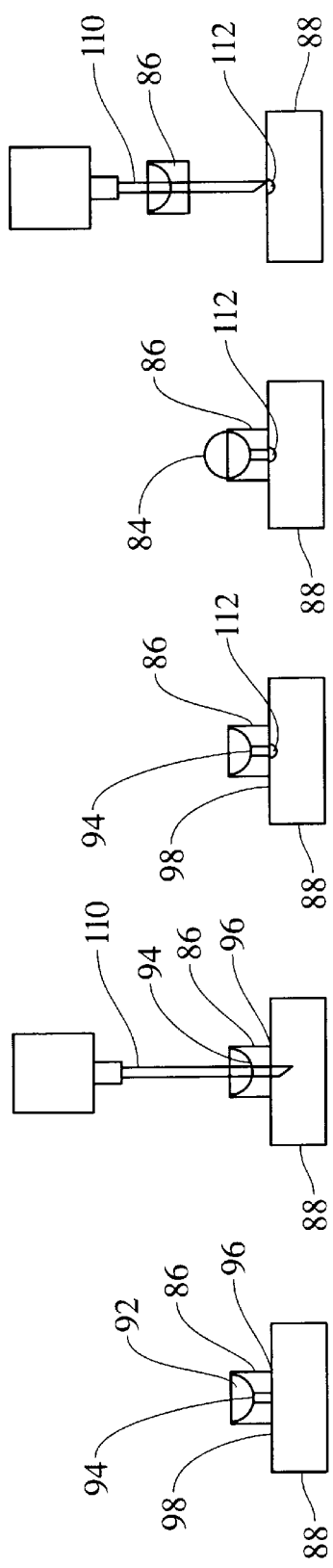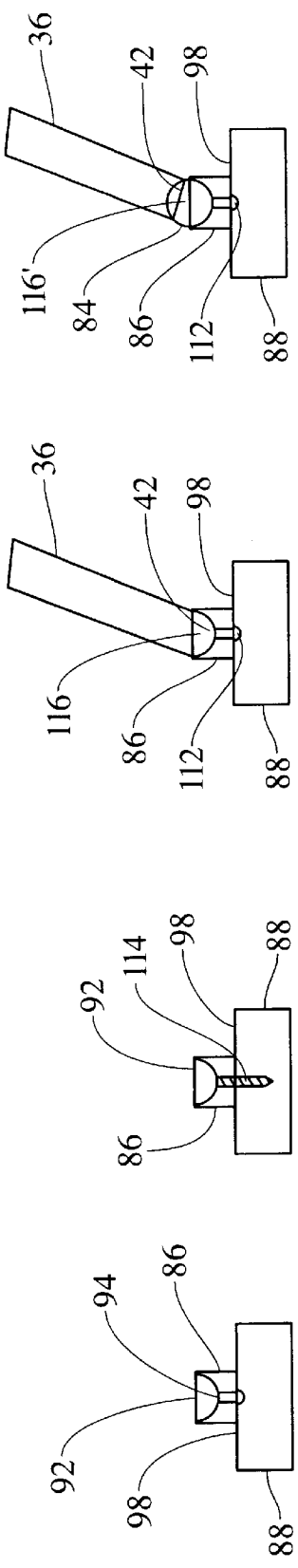

FIDUCIAL POSITIONING CUP

BACKGROUND OF THE INVENTION

The present invention relates to the medical diagnostic and surgical arts. It finds particular application in conjunction with stereotactic surgery and will be described with particular reference thereto. However, it is to be appreciated that the invention will also find application in conjunction with minimally invasive surgery, neurosurgery, neurobiopsy, CT-table needle body biopsy, breast biopsy, endoscopic procedures, orthopedic surgery, other invasive medical procedures, industrial quality control procedures, and the like.

Three-dimensional diagnostic image data of the brain, spinal cord, and other body portions are produced by CT scanners, magnetic resonance imagers, and other medical diagnostic equipment. These imaging modalities typically provide structural detail with a resolution of one millimeter or better. Various frameless stereotaxy procedures have been developed which take advantage of three-dimensional image data of the patient. These procedures include guided-needle biopsies, shunt placements, craniotomies for lesion or tumor resection, and the like. Another area of frameless stereotaxy procedure which requires extreme accuracy is spinal surgery including screw fixation, fracture decompression, and spinal tumor removal.

In brain biopsy procedures, for example, surgeons or other medical personnel drill and tap a hole in a patient's skull. Surgeons have come to rely on frameless stereotaxy procedures for placing and orienting the bit of the surgical drill prior to forming the hole in the skull. These procedures require aligning images of fiducials or markers, affixed at three or more spaced points on the patient's body, with known fiducial positions in patient space. The fiducials are spherical markers or small beads that are injected with radiation opaque and magnetic resonance excitable materials and fit within a fiducial positioning cup. Therefore, the fiducials are visible in the imaging medium selected such that they show up as readily identifiable dots in the resultant image data.

Heretofore, the fiducials have been affixed directly to the patient's body using a glue. Fiducials have also been attached to a patient's skull using screws. However, these methods of attachment have proven undesirable, especially if it is necessary to remove,the fiducials for a period of time before they are reattached. Because the imaging modalities discussed above typically provide structural detail with a resolution of a millimeter or better, it is critical that the fiducials be reattached as close as possible to the exact location where they were previously located. Such accuracy is difficult to achieve when using a glue to attach the small, spherical fiducials directly to the patient's body.

The present invention provides a new and improved apparatus and method which overcomes the above-referenced problems and others.

SUMMARY OF THE INVENTION

A fiducial cup for a magnetic resonance imaging system for designating a coordinate and trajectory on a subject includes a subject support. A frame assembly mounts at least two receivers in a fixed relationship to the subject. A wand defines a tip portion and a pointing axis of the wand. At least two wand emitters are mounted in a spaced relationship in a fixed relationship to the pointing axis and the tip. The emitters selectively emit wand signals which are received by the at least two receivers. A wand position processor determines a position of the wand tip portion from the wand signals from the wand emitters which are received by the at least two receivers. An image memory stores image data indicative of a three-dimensional region of the portion of the subject which is secured to the subject support means. A selecting means selects data from the three-dimensional image memory. A display converts the selected data from the image memory into human-readable displays. A transform processor transforms a position of the wand tip and trajectory into a coordinate system of the image data stored in the image memory. At least three fiducials are imaged during generation of the image data. The fiducials are disposed at selected subject positions when the three-dimensional image data is acquired such that locations of the three fiducials are identifiable in the three-dimensional image data. The fiducials are supported by fiducial cups. Each fiducial cup comprises a fiducial receiving surface against which the fiducial is removably mounted. A subject surface is removably affixed to the subject.

In accordance with one aspect of the invention, the fiducial receiving surface includes a hemispherical well.

In accordance with a more limited aspect of the invention, a central bore extends from a bottom of the hemispherical well to the subject surface.

In accordance with another aspect of the invention, the fiducial receiving surface has a spherical segment well of a common radius with the wand tip for rotatably receiving the wand tip therein.

In accordance with another aspect of the invention, an adhesive secures the subject surface to the subject and a fiducial to the fiducial surface.

In accordance with a more limited aspect of the invention, a screw extends through the central bore for attachment to the subject.

One advantage of the present invention is that it improves the accuracy of positioning and repositioning of fiducials.

Another advantage of the present invention is that it improves the accuracy with which the diagnostic images are aligned with the patient.

Another advantage of the present invention is that the fiducials are securely held within the fiducial positioning cups.

Another advantage of the present invention is that the fiducial positioning cups include a larger surface area, relative to the fiducials, for contacting to the patient's skin.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 5 illustrates a fiducial positioning cup on the surface of a patients skin;

FIG. 7 illustrates a needle inserted through the fiducial cup for tattooing a mark in the patient's skin;

FIG. 8 illustrates a fiducial positioning cup having a tattooed mark below the bore;

FIG. 9 illustrates the fiducial inserted into the fiducial positioning cup;

FIG. 10 illustrates the needle aligned with the tattooed mark for repositioning the fiducial cup;

FIG. 11 illustrates the repositioned fiducial cup held in place by adhesive;

FIG. 12 illustrates the fiducial cup held in place by a screw;

FIG. 13 illustrates a convex hemispherical wand tip placed in the fiducial cup; and FIG. 14 illustrates a concave hemispherical wand tip placed on a spherical fiducial held in the fiducial cup.

DETAILED DESCRIPTION OF THE PREFERRED EMBODIMENTS

Figure 1:
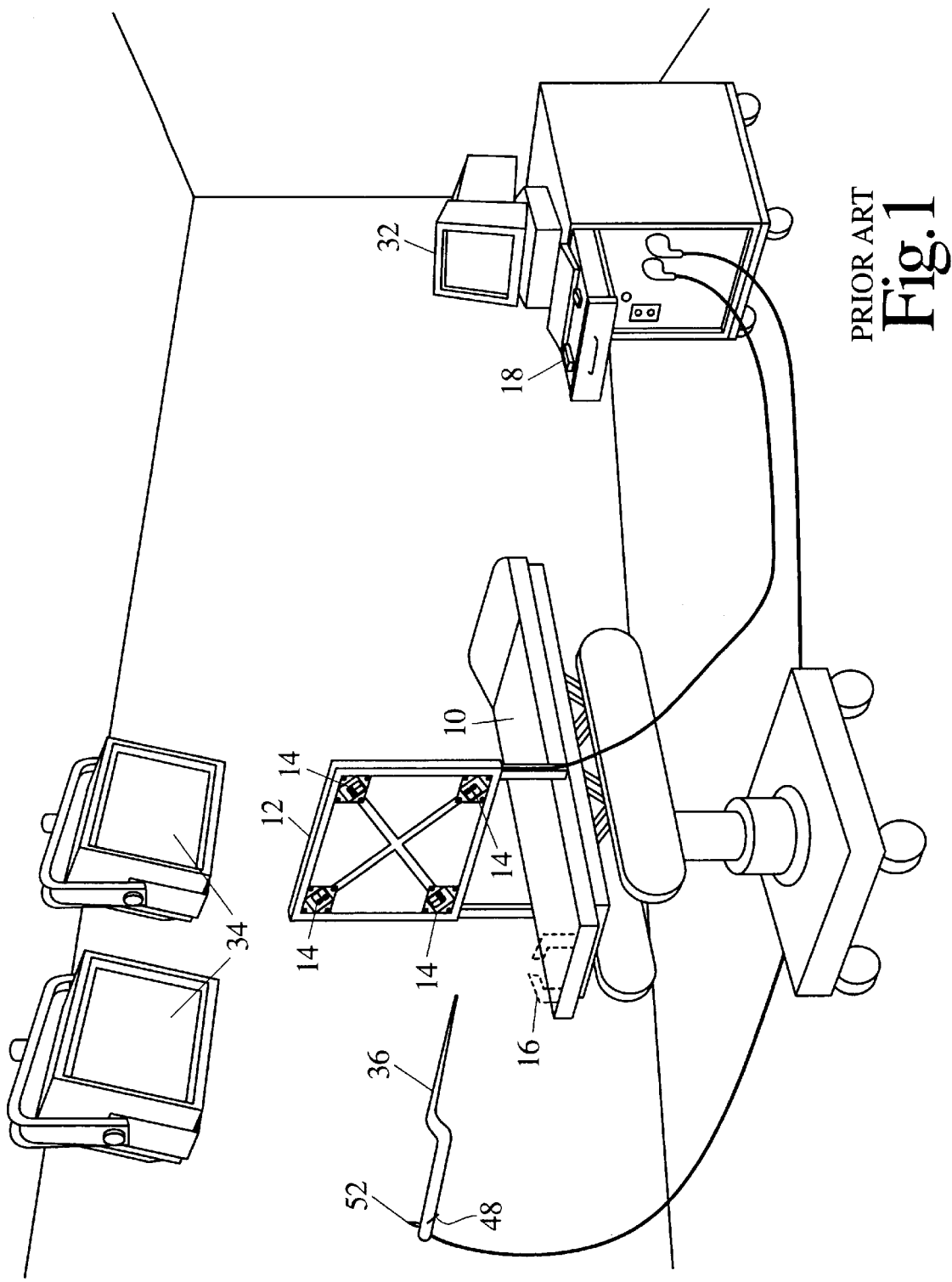
FIG. 1 is a perspective view of an operating room in which the present invention is deployed.

With reference to FIG. 1, a subject, such as a human patient is received on an operating table or other subject support 10 and appropriately positioned within the operating room. A frame 12 is mounted in a fixed relationship to the patient such that it is precisely positioned within the subject or subject support coordinate system. In the illustrated embodiment, the frame 12 is mounted to the patient support 10. Mounting the frame 12 to the patient support 10 permits the support to be turned, raised, lowered, wheeled to another location, or the like, without altering the patient coordinate system. Alternatively, the support may be mounted to a pole or other stationary support, the ceiling of the room, or the like. The frame 12 supports a plurality of receivers 14 such as microphones, radio frequency receivers, light sensitive diodes, other light sensitive receivers, and the like mounted at fixed, known locations thereon. A securing means, such as a head clamp 16, securely positions a portion of the subject into the frame of reference of the frame 12.

Figure 2:
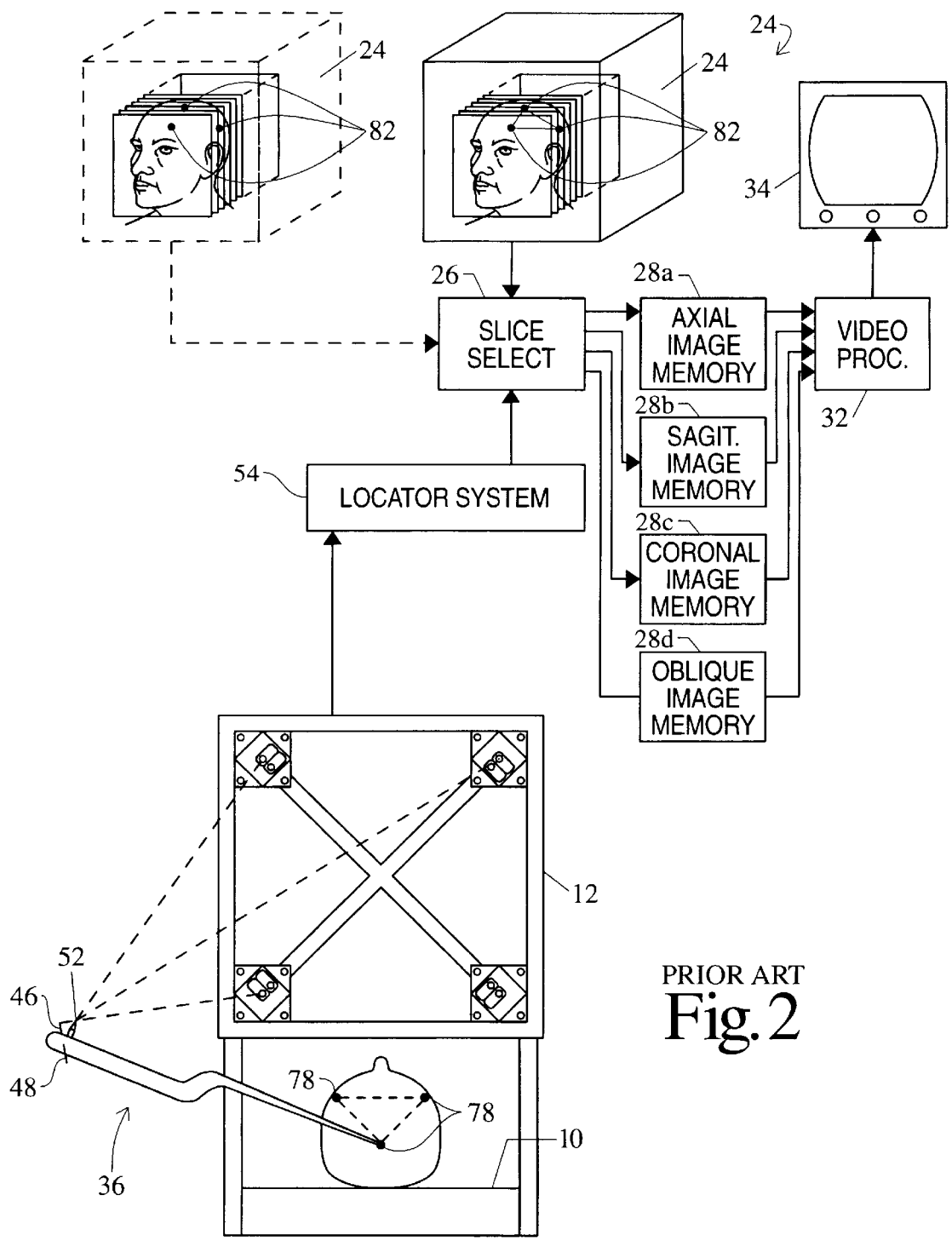
FIG. 2 is a block diagram of the image data manipulation of the present system of FIG. 1.

With continuing reference to FIG. 1 and further reference to FIG. 2, an operator console 18 houses a computer system 22 and a data memory 24. The stored three-dimensional image data preferably contains a video pixel value for each voxel or point in a three-dimensional rectangular grid of points, e.g. a 256×256×256 grid. Selectable orthogonal and other oblique planes of the data can readily be withdrawn for display from the three-dimensional memory 24 by a plane or slice selector 26 using conventional technology.

For example, the pixel values which lie on a selected axial, sagittal, coronal, and oblique planes are copied into corresponding image memories 28a, 28b, 28c, 28d. A video processor 32 converts the two-dimensional digital image representations from one or more of the image memories 28 into appropriate signals for display on video monitors 34 or other appropriate image displays.

Figure 3:
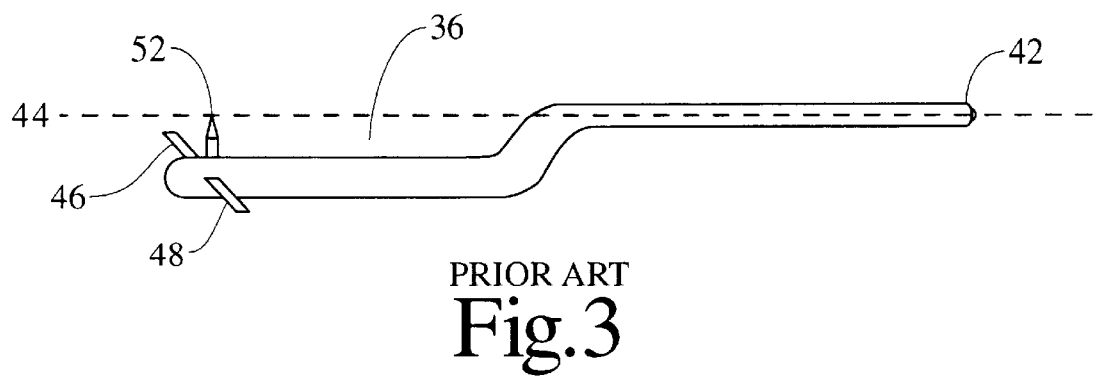
FIG. 3 illustrates the wand.

With continuing reference to FIG. 1 and further reference to FIG. 3, a wand 36, formed of suitable material such as metal, has a hemispherical tip portion at a proximal end 42. The tip is connected to a portion extending along a pointing axis 44 of the wand. In the illustrated embodiment, a first emitter 46 is located at $(x_1, y_1, z_1)$ along the axis 44 a fixed known distance $l_1$ from the tip 42. The second emitter 48 is at $(x_1+\Delta x_2, y_1+\Delta y_2, z_1+\Delta z_2)$, where $\Delta x_2$, $\Delta y_2$ and $\Delta z_2$ represent constant values based on the geometry of the second emitter 48 relative to the tip 42. The third emitter 52 is at $(x_1+\Delta x_3, y_1+\Delta y_3, z_1+\Delta z_3)$, where $\Delta x_3$, $\Delta y_3$ and $\Delta z_3$ represent constant values based on the geometry of the third emitter 52 relative to the tip 42.

Emitters 46, 48, 52 emit infra-red positioning signals used by a locator system 54 to locate a coordinate and trajectory of the wand. Infra-red signals are received from each of the emitters at the two receivers. The three infrared signals received by each receiver are used to calculate the axis 44 and the location of the tip. The plane or slice selector 26 (FIG. 2) selects patient image planes based on the coordinate and trajectory located. It is to be appreciated that more than three emitters, may be mounted on the wand to provide additional positioning signals to be used by a locator system to locate the coordinate and trajectory of the wand. Furthermore, it is to be Understood that the emitters 46, 48, 52 may also emit spark or radio frequency signals which are received by the receivers 14.

Figure 4:
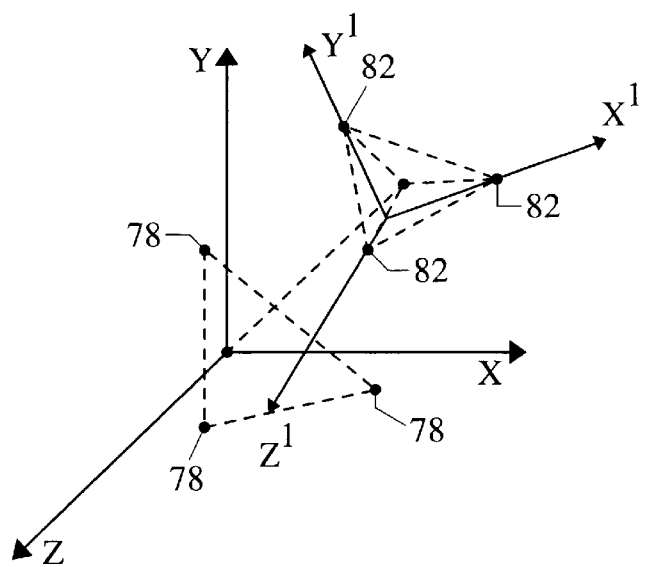
FIG. 4 is illustrative of a preferred coordinate transform between the coordinate system of the data and the patient.

With reference to FIG. 4, before the wand 36 can be used to locate a proper coordinate and trajectory for a surgical tool such as a drill, the patient ;pace or coordinate system (x, y, z) is aligned with the image space or coordinate system (x', y', z') stored in memory. Aligning the spaces begins with referencing known positions or points 78 in the patient space with the wand tip 42. For example, the tip of the wand may be referenced to three fiducials, tattoo marks, or characteristic physical anatomy, e.g. the tips of the spinous and traverse processes. These known points 78 are compared with corresponding position of pixels 82 in the image space.

Figure 6:
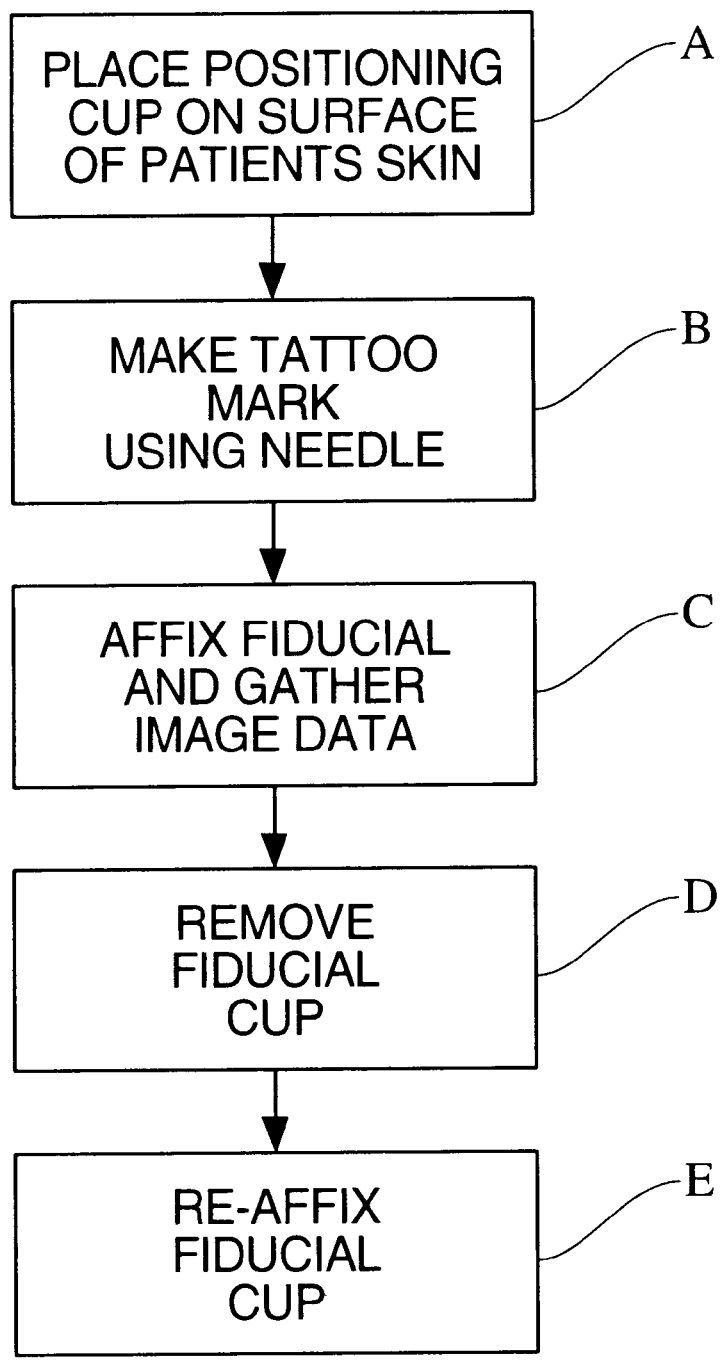
FIG. 6 illustrates the steps of positioning and repositioning a fiducial positioning cup and a fiducial.

With reference to FIGS. 5 and 6, a positioning cup 86 is placed on the surface of the patient's skin 88 in a step A. Each positioning cup 86 is a base into which one of the fiducials 84 is attached. Furthermore, the cups 86 each have a hemispherical (or slightly less than a half sphere) well 92 in its top and a central bore 94 from the bottom of the hemisphere 92 to a base 96 of the cup. The fiducial positioning cup 86 is preferably invisible to the imaging medium selected such that it does not show up in the resultant image data. Preferably, the positioning cup 86 is glued to the patient's skin 88.

As described above, image data, including the fiducials affixed at the three or more spaced points on the patient's body, is aligned with the patient space containing physical fiducials 84. Therefore, the fiducials 84 and the positioning cups 86 ideally remain fixed in place during the time interval between which the image data is gathered and the stereotaxy procedure is performed. However, because this time interval may be several hours, or even days, the cups are not always kept in place. Rather, they are removed and reattached later.

To facilitate accurately repositioning the cups 86, FIGS. 6 and 7 illustrate that in a step B, before the fiducials 84 are attached in the cup or after the fiducials are removed from the cup, a tattoo needle 110 is inserted through the bore 94 to place a small tattoo mark 112 (see FIG. 8) on the patient's skin 88. Thereafter, in a step C the fiducial 84 is affixed to the support (see FIGS. 6 and 9), preferably using adhesive, and the image data is gathered. After the image data is obtained, the positioning cups 86 are removed in a step D of FIG. 6. The tattoo marks 112, however, remain visible.

Before the stereotaxy procedure is performed, the three cups 86 are re-affixed to the patient's skin 88 in a step E of FIG. 6. With reference to FIG. 10, the needle 110 is inserted through the central bore 94 of a fiducial positioning cup 86 to be secured. The tip of the needle 110 is then placed on the mark 112 on the subject. The fiducial positioning cup 86 is then slid along the needle 110 until it contacts the patients skin 88. Because the tip of the needle 110 is located in the tattooed spot 112, the support 86 is accurately positioned so that it is centered on the tattooed spot 112. Preferably, as illustrated in FIG. 11, the fiducial positioning cups 86 are then secured to the subject. Alternatively, as illustrated in FIG. 12, a surgical screw 114 is inserted into the respective bore to affix' the fiducial support 86 to the patient's skull or other boney plate.

As already discussed above in reference to FIG. 4, the positions of the three fiducials 84 are compared with the relative position of the images 82 of the centroids of the fiducials in the image space. Actuating the emitters while the tip of the wand is touching each of its characteristic patient space points (x, y, z) defines these points electronically. Like coordinates (x', y', z') of the image pixels 82 are defined electronically from the electronic image and compared to the patient space coordinates (x, y, z). As illustrated in FIG. 13, the wand 36 preferably has a convex hemispherical end which is inserted into each of the respective fiducial supports 86. After the emitters are actuated, a virtual tip 116 of the wand is then correlated with a centroid of the fiducial in the electronic image. The virtual tip is defined at the geometric center of the sphere defined by the hemispherical tip. Because the hemispherical tip 42 of the wand is the same radius as the fiducial 84, the virtual tip 116 of the wand is located at the centroid of the fiducial, regardless of the wand's trajectory.

As illustrated in FIG. 14, in an alternative embodiment, the wand 36 has a concave partial spherical in its tip 42 which contacts the spherical surface of the fiducial 84. In this embodiment, the virtual tip 116' of the wand is calculated to be the geometric center of the partial spherical surface which falls at the centroid of the fiducial when the tip is against the fiducial. In either of the two embodiments, the virtual tip of the wand is offset from the physical tip.

Having aligned the image and patient spaces, a wand with its physical and virtual tips aligned can be used to identify the entry coordinate and trajectory at which the surgical tool will be applied to the patient. The surgeon maneuvers the wand to a proposed trajectory and actuates the emitters. Signals from the emitters are used to calculate the trajectory and the end point of the wand. The trajectory and end point are displayed on the monitor superimposed on the three-dimensional image or selected image plane(s).

By viewing the display, the surgeon identifies the location of the wand tip with respect to anatomic structure, and the trajectory of the bore. If the trajectory is unsatisfactory, the wand is repositioned and its new trajectory determined and evaluated.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A fiducial cup for a magnetic resonance imaging system for designating a coordinate and trajectory on a subject which includes a subject support, a frame assembly which mounts at least two receivers in a fixed relationship to the subject, a wand defining a tip portion and a pointing axis of the wand, and having at least two wand emitters mounted in a spaced relationship in a fixed relationship to the pointing axis and the tip, the emitters selectively emitting wand signals which are received by the at least two receivers, a wand position processor for determining a position of the wand tip portion from the wand signals from the wand emitters which are received by the at least two receivers, an image memory for storing image data indicative of a three-dimensional region of the portion of the subject which is secured to the subject support means, a selecting means for selecting data from the three-dimensional image memory, a display for converting the selected data from the image memory into human-readable displays, a transform processor for transforming a position of the wand tip and trajectory into a coordinate system of the image data stored in the image memory, at least three fiducial markers which are imaged during generation of the image data disposed at selected subject positions when the three-dimensional image data was acquired such that locations of the three fiducial markers are identifiable in the three-dimensional image data, each of the fiducial markers being supported by a respective fiducial cup, each fiducial cup comprising:

a fiducial receiving cup having a hemispherical well, a fiducial marker, including an imageable material, being removably secured in the hemispherical well, the hemispherical well of the fiducial receiving cup and the fiducial marker having a common centroid, and the hemispherical well being accessible and defining a concave bearing surface when the fiducial marker is removed; and a subject surface that is adapted to be removably affixed to a subject.

2. A fiducial cup, comprising:

a fiducial receiving surface defining a hemispherical well for removably receiving a fiducial which includes an imageable material which is imaged in a diagnostic imaging procedure;

a subject surface that removably engages a subject;

a central bore extending from a bottom of the hemispherical well to the subject surface; and a screw extending through the central bore for attachment to the subject.

3. An apparatus for correlating a physical subject with diagnostic images of the physical subject, the apparatus comprising:

at least three fiducial cups, each fiducial cup including a subject surface, adapted to be secured to a physical subject, and a fiducial receiving surface;

a fiducial marker received in the fiducial receiving surface of said each fiducial cup, said each fiducial marker being spherical and containing an imageable material such that said each of the fiducial markers is imaged in diagnostic images;

a pointer having a tip portion including a spherical well of a common radius with said each fiducial marker which is selectively movable to be touched to each of the fiducial markers; and an electronic circuit for correlating the pointer with the diagnostic images, the physical subject being correlated with the diagnostic images after the pointer is touched to at least three of the fiducial markers.

4. The apparatus as set forth in claim 3 wherein the imageable material has a physical mass which is centered on a geometric center of the respective fiducial marker, the tip of the pointer being offset from the physical center by a radius of the respective fiducial marker.

5. The apparatus as set forth in claim 4, wherein the pointer has a virtual tip offset from its physical tip by the common radius, such that when said each fiducial marker is received in the concave well of the tip, the virtual tip and the geometric center of the fiducial coincide.

6. The apparatus as set forth in claim 4, wherein the pointer tip includes a spherical end segment of common radius with said each fiducial marker and defines a virtual tip in an interior of the physical tip the common radius from a surface of the spherical segment, such that when the tip is positioned in the fiducial surface of the fiducial cup in the absence of one of the fiducial markers, the virtual tip coincides with the physical center of one of the fiducial markers.

7. The apparatus as set forth in claim 3, wherein the fiducial cup includes a central bore extending between the fiducial surface and the subject surface.

8. A method of correlating locations on a subject with a diagnostic image, the method comprising:
   a) identifying at least three locations on a subject;
   b) attaching fiducial positioning cups to the at least three locations on the subject;
   c) securing respective fiducials to each of the at least three fiducial positioning cups, each fiducial positioning cup including a central bore and defining a well which is shaped to receive the respective fiducials;
   d) performing a diagnostic imaging procedure to generate a diagnostic image, the fiducials being identifiable in the diagnostic image;
   e) correlating locations on the subject with the diagnostic image;
   f) removing the fiducials from the subject; and
   g) marking the subject by passing a marker through the central bore such that the marker contacts the subject, the mark providing a reference for repositioning the fiducial positioning cups.

9. A method of correlating locations on a subject with a diagnostic image, the method comprising:
   a) identifying at least three locations on a subject;
   b) marking the subject to identify the at least three locations at which fiducial positioning cups are to be secured on the subject;
   c) attaching the fiducial positioning cups to the at least three locations on the subject, including:
      c1) inserting a needle through a central bore of each of the fiducial positioning cups to be secured;
      c2) placing a tip of the needle on the mark on the subject; and
      c3) sliding the fiducial positioning cup along the needle;
   d) securing respective fiducials to each of the at least three fiducial positioning cups, the fiducial positioning cups defining a well which is shaped to receive the respective fiducials;
   e) performing a diagnostic imaging procedure to generate a diagnostic image, the fiducials being identifiable in the diagnostic image;
   f) correlating locations on the subject with the diagnostic image; and
   g) removing the fiducials from the subject.

10. A method of correlating locations on a subject with a diagnostic image of the subject, the method comprising:
    a) identifying at least three locations on a subject;
    b) attaching respective subject surfaces of fiducial positioning cups to the at least three locations on the subject;
    c) securing respective spherical fiducials to respective fiducial receiving surfaces of each of the at least three fiducial positioning cups, the fiducial receiving surfaces defining wells which are shaped to receive the respective spherical fiducials;
    d) performing a diagnostic imaging procedure to generate a diagnostic image, the fiducials being identifiable in the diagnostic image;
    e) correlating locations on the subject with the diagnostic image, including:
       e1) selectively touching a tip of a stereotactic tool to each of the fiducials, the tip having a common radius with each of the fiducials; and
       e2) correlating physical locations of the stereotactic pointer with the diagnostic images using an electronic circuit; and
    f) removing the fiducials from the subject.

11. A method of correlating locations on a subject with a diagnostic image, the method comprising:
    a) identifying at least three locations on a subject;
    b) marking the subject to identify the at least three locations at which fiducial positioning cups are to be secured on the subject;
    c) attaching respective subject surfaces of the fiducial positioning cups to the at least three locations on the subject, including:
       c1) inserting a needle through a central bore of each of the fiducial positioning cups to be attached;
       c2) placing a tip of the needle on the mark on the subject; and
       c3) sliding the fiducial positioning cup along the needle;
    d) securing respective fiducials to respective fiducial receiving surfaces of each of the at least three fiducial positioning cups, the fiducial receiving surfaces defining a hemispherical well which is shaped to receive the respective fiducials;
    e) performing a diagnostic imaging procedure to generate a diagnostic image, the fiducials being identifiable in the diagnostic image;
    f) correlating locations on the subject with the diagnostic image;
    g) removing the fiducials from the subject;
    h) defining a virtual point on a stereotactic tool, which virtual point is displaced from a physical point of a stereotactic pointer by a characteristic distance, the stereotactic pointer having a tip with a substantially same shape as each of the fiducials, the well in each of the fiducial positioning cups being shaped to also receive the stereotactic pointer tip, each of the fiducials containing a material including a characteristic point which is imaged during the imaging process and which appears in the diagnostic image, the characteristic point being displaced from a surface of the fiducial by a characteristic distance;
    i) after performing the diagnostic imaging procedure, removing each of the fiducials from the respective fiducial positioning cups; and
    j) inserting the stereotactic pointer tip in the fiducial positioning cups, such that the virtual tip is coincident with the position which was occupied by the characteristic portion of the respective fiducial before the respective fiducial was removed.

12. A fiducial cup, comprising:
    a fiducial receiving cup defining an open well surrounded by a curved bearing surface that defines a cup bearing surface centroid, the cup bearing surface being contoured for selectively receiving a bearing surface of a tool and registering the tool relative to the cup bearing surface centroid;

a fiducial containing an imageable material surrounding an imageable material centroid, the bearing surface centroid and the imageable material centroid being coincident when the fiducial is removably mounted in the well for imaging in a diagnostic imaging procedure; and a subject surface that is adapted to be removably affixed to a subject.

13. The fiducial cup as set forth in claim 12, further including:

a central bore extending from a bottom of the well to the subject surface.

14. The fiducial cup as set forth in claim 12, wherein the cup bearing surface of the fiducial receiving cup includes a spherical segment well of a common radius with the bearing surface of the tool.

15. The fiducial cup as set forth in claim 12, further including:

an adhesive which removably secures both the subject surface to the subject and the fiducial to the fiducial receiving cup.

16. The fiducial cup as set forth in claim 12, wherein the cup bearing surface is hemispherical for receiving a spherical fiducial.

* * * * *